United States Patent
Park

(10) Patent No.: US 10,513,689 B2
(45) Date of Patent: Dec. 24, 2019

(54) CULTURE MEDIA FOR MULTIPOTENT STEM CELLS

(71) Applicant: Hope Biosciences LLC, Houston, TX (US)

(72) Inventor: Hyeonggeun Park, Sugar Land, TX (US)

(73) Assignee: HOPE BIOSCIENCES, LLC, Sugar Land, TX (US)

(*) Notice: Subject to any disclaimer, the term of this patent is extended or adjusted under 35 U.S.C. 154(b) by 13 days.

(21) Appl. No.: 15/142,135

(22) Filed: Apr. 29, 2016

(65) Prior Publication Data

US 2017/0313985 A1 Nov. 2, 2017

(51) Int. Cl.
*C12N 5/0775* (2010.01)
*C12N 5/077* (2010.01)

(52) U.S. Cl.
CPC ......... *C12N 5/0667* (2013.01); *C12N 5/0653* (2013.01); *C12N 5/0654* (2013.01); *C12N 5/0655* (2013.01); *C12N 2500/25* (2013.01); *C12N 2500/32* (2013.01); *C12N 2500/84* (2013.01); *C12N 2500/90* (2013.01); *C12N 2501/11* (2013.01); *C12N 2501/21* (2013.01); *C12N 2501/30* (2013.01); *C12N 2501/999* (2013.01); *C12N 2506/1384* (2013.01)

(58) Field of Classification Search
CPC .. C12N 5/0667; C12N 5/0653; C12N 5/0654; C12N 5/0655; C12N 2500/25; C12N 2500/32; C12N 2500/84; C12N 2500/90; C12N 2501/11; C12N 2501/21; C12N 2501/30; C12N 2501/999; C12N 2506/1384
USPC ....................................................... 435/326
See application file for complete search history.

(56) References Cited

U.S. PATENT DOCUMENTS

| 5,968,829 | A | 10/1999 | Carpenter | |
| 7,807,461 | B2 | 10/2010 | Kang et al. | |
| 8,252,591 | B2 * | 8/2012 | Ince | C12N 5/0631 435/383 |
| 8,835,175 | B2 | 9/2014 | Cervantes | |
| 2004/0037811 | A1 * | 2/2004 | Penn | A61K 35/28 424/93.7 |
| 2007/0128685 | A1 | 6/2007 | Faudoa et al. | |
| 2008/0085555 | A1 * | 4/2008 | Asahara | C12N 5/0647 435/366 |
| 2010/0003265 | A1 * | 1/2010 | Scheffler | C12N 5/0693 424/174.1 |
| 2011/0171726 | A1 | 7/2011 | Kang et al. | |
| 2015/0064273 | A1 | 3/2015 | Peled | |

FOREIGN PATENT DOCUMENTS

| CN | 103255103 | 8/2013 |
| WO | WO 2008/020815 | 2/2008 |
| WO | WO 2013/121427 | 8/2013 |
| WO | WO 2015/186906 | 12/2015 |

OTHER PUBLICATIONS

Broxmeyer et al., Stromal cell-derived factor-1/CXCL12 directly enhances survival/antiapoptosis of myeloid progenitor cells through CXCR4 and Gαi proteins and enhances engraftment of competitive, repopulating stem cells, Journal of Leukocyte Biology, vol. 73, May 2003, pp. 630-638.*
Kortesidis et al., Stromal-derived factor-1 promotes growth, survival, and development of human bone marrow stromal stem cells, Blood, vol. 105, No. 10 (2005), pp. 3793-3801.*
Colleoni et al., "Isolation, growth and differentiation of equine mesenchymal stem cells: effect of donor, source, amount of tissue and supplementation with basic fibroblast growth factor", *Vet Res Commun*. 33(8):811-21 (2009).
Furge et al., "Met receptor tyrosine kinase: enhanced signaling through adapter proteins", Oncogene 19:5582-5586 (2000).
Kang et al., "Role of c-Jun N-terminal kinase in the PDGF-induced proliferation and migration of human adipose tissue-derived mesenchymal stem cells", *J Cell Biochem* 95: 1135-1145 (2005).
Krampera et al., "HB-EGF/HER-1 signaling in bone marrow mesenchymal stem cells: inducing cell expansion and reversibly preventing multilineage differentiation", *Blood*, 106:59-66 (2005).
Pons et al., "VEGF improves survival of mesenchymal stem cells in infarcted hearts", *Biochem Biophys Res Commun* 376:419-422 (2008).
Tamama et al., "Epidermal growth factor (EGF) treatment on multipotential stromal cells (MSCs). Possible enhancement of therapeutic potential of MSC", *J Biomed Biotechnol* 10.1155/2010/795385 (2010).
Tamama et al., "Epidermal growth factor as a canidate for ex vivo expansion of bone marrow-derived mesenchymal stem cells", *Stem Cells*, 24:686-695 (2006).

* cited by examiner

*Primary Examiner* — Jennifer M. H. Tichy
(74) *Attorney, Agent, or Firm* — Rao DeBoer Osterrleder, PLLC; Dileep P. Rao

(57) ABSTRACT

A culture medium for human adipose tissue derived mesenchymal stem cells includes a keratinocyte-SFM basal medium, L-Cysteine, FGF and SDF-1 is disclosed. The culture medium is effective for growing mesenchymal stem cells at a high proliferation rate while maintaining the purity, characterization and undifferentiated state of the cells.

19 Claims, 5 Drawing Sheets

FIG. 1, Continued
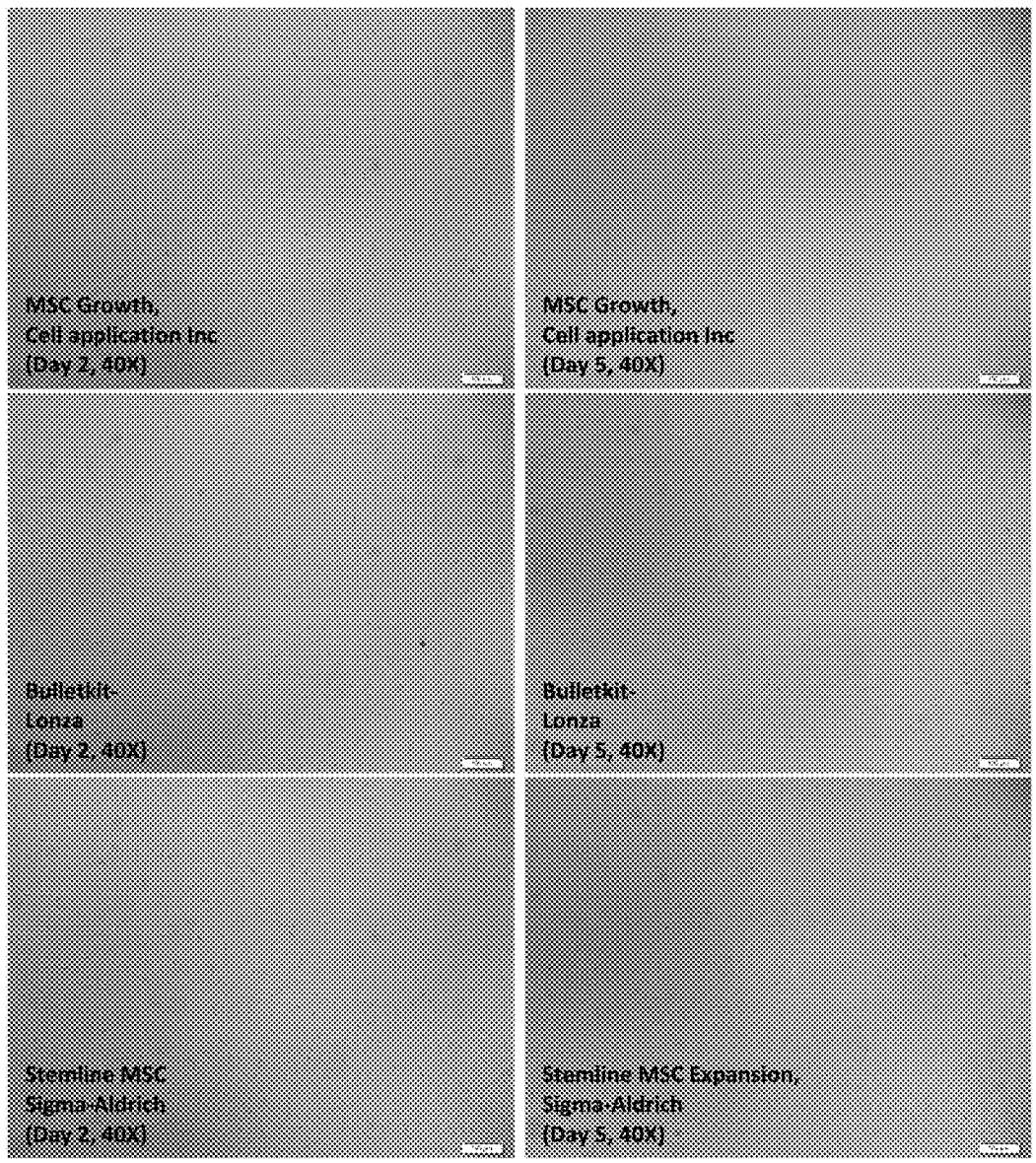

FIG. 1, cont'd
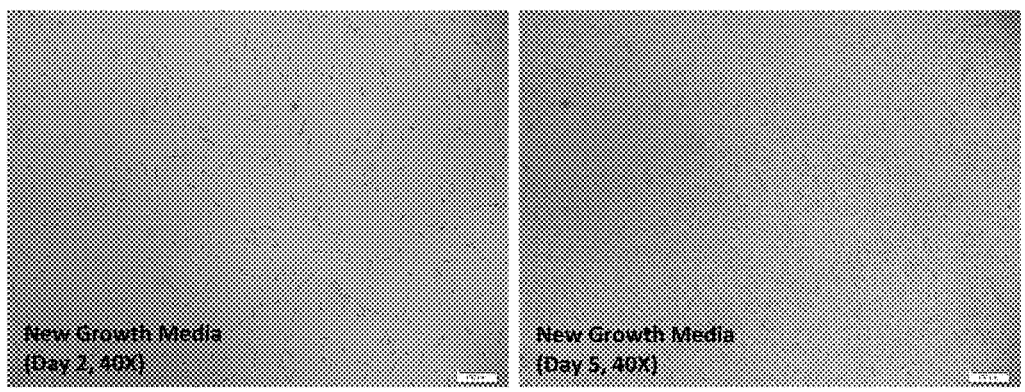
FIG. 2
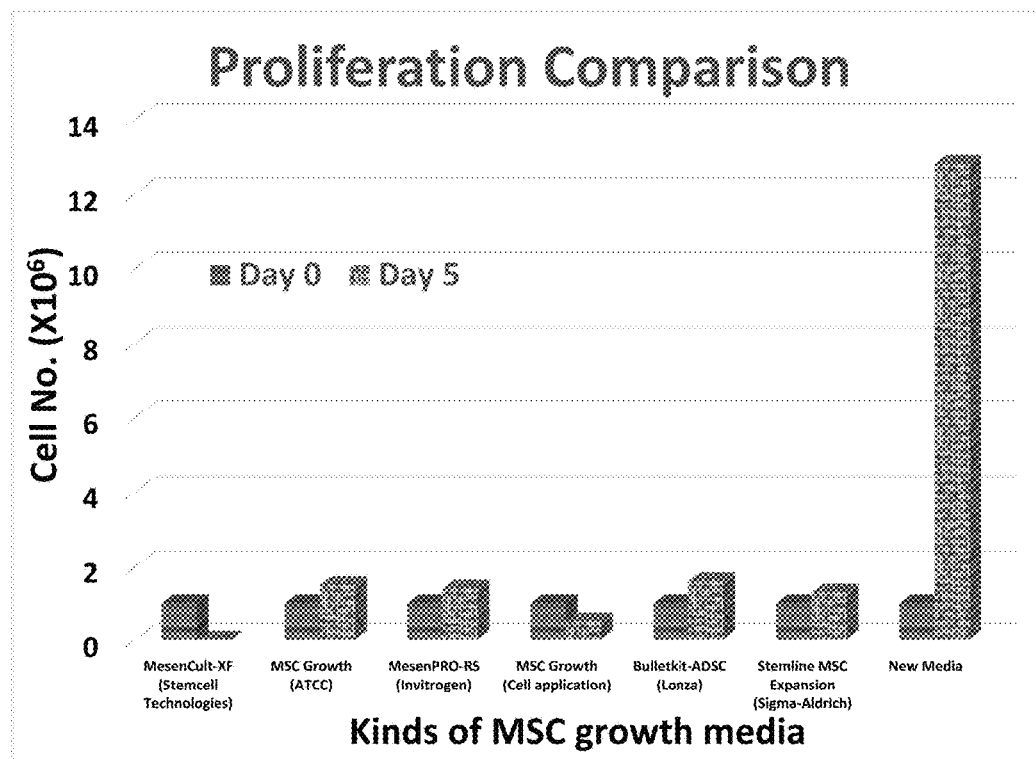

CULTURE MEDIA FOR MULTIPOTENT STEM CELLS

BACKGROUND OF THE DISCLOSURE

Stem cells are cells that have the potential to develop into different cell types in the body during early life and growth. They have the ability to self-renew and are integral in the body's natural repair process. There are two primary sources of stem cells, embryonic and non-embryonic or adult stem cells. Adult stem cells are found in practically every tissue or organ in the body. They too have the ability to self-renew and differentiate into a multitude of specialized cell types.

Mesenchymal stem cells (MSCs) are a specific group of mesoderm origin adult stem cells that are pluripotent. Being pluripotent, they have multi-directional differentiation capabilities. They can become fat, bone, cartilage, tendons, muscle, nerves, ligaments, liver, cardiac muscle, endothelial cells, pancreatic islet cells and many others. In addition, they are cells with low immunogenicity and are naturally immune-modulatory cells. Given their versatility, MSCs have quickly become an ideal cell type used in therapeutics for degenerative and autoimmune conditions.

MSCs have the unique ability to navigate or home to areas of injury and/or degeneration. When the body is in need of repair it sends out signals to mobilize the stem cells to begin the repair process. MSCs not only differentiate but increase angiogenesis and excrete anti-inflammatory cytokines and growth factors. MSCs were originally found in bone marrow. It was soon discovered that in elderly or ill adults, the MSC content in bone marrow is extremely low. Low stem cell yield and a painful donation process led scientists to look for other, more easily available sources of MSCs in the body. This search led them to fat tissue.

Adipose tissue contains approximately 100,000 MSCs per gram of fat (Sen et al., 2001). It is a naturally rich source of MSCs and they are mostly unaffected by age or the donor's condition. Fat is becoming very popular as a stem cell source because of its ease in extraction and in most cases, ample availability.

Having a large amount of fat tissue may translate into a high stem cell count but acquiring a large amount is a fairly invasive procedure. Liposuction often requires general anesthesia and vacuum suction. When machine suction is used, cells are often broken and injured during the extraction process. Therefore, small, localized syringe extractions are ideal. In this case, a 5 gram extraction would yield approximately 500,000 MSCs. To reach therapeutic quantities of MSCs (in the millions or billions), in vitro cell culture is a typical solution.

Culturing fat derived MSCs is much easier compared to other sources. They generally proliferate well and behave consistently regardless of the donor's age or condition. However, their proliferative potential and their stem cell characteristics are continuously decreased during prolonged culture. For example, it has been shown that expansion in culture leads to premature senescence (the process of aging characterized by continuous morphological and functional changes). Cells became much larger with irregular and flat shape and the cytoplasm became more granular. These senescence-associated effects are continuously acquired from the onset of in vitro culture (Wagner et al., 2008). As a result, the successful manufacturing for commercialization of large batches from one donor of homogenous MSCs that preserve their characteristics following expansion in culture remains a challenge.

Methods for increasing proliferation and survival in MSCs have been widely studied over the past few years and many factors have been proposed for increasing the expansion efficiency of these cells. For example, many protocols relating to the expansion of MSCs include culturing in the presence of basic fibroblast growth factor (b-FGF) (Colleoni et al., 2009). It has been shown that b-FGF not only maintains MSC proliferation potential, it also retains osteogenic, adipogenic and chondrogenic differentiation potentials through the early mitogenic cycles. Vascular endothelial growth factor (VEGF) has also been shown to increase MSC proliferation (Pons et al., 2008). Hepatocyte growth factor (HGF) has been shown to affect proliferation, migration and differentiation (Furge et al., 2000). Platelet derived growth factor (PDGF) shown to be a potent mitogen of MSCs (Kang et al., 2005). Epidermal growth factor (EGF) and heparin-binding EGF have both been shown to promote ex vivo expansion of MSCs without triggering differentiation into any specific lineage (Tamama et al., 2006; Krampera et al., 2005). In addition to its mitogenic effect on MSCs, EGF also increases the number of colony-forming units by 25% (Tamama et al., 2010).

SUMMARY OF THE DISCLOSURE

Thus, in accordance with the present disclosure, there is provided a stem cell growth medium comprising:
 (a) serum;
 (b) fibroblast growth factor;
 (c) epidermal growth factor;
 (d) hydrocortisone;
 (e) calcium chloride;
 (f) insulin;
 (g) bovine pituitary extract;
 (h) L-cysteine or glutathione;
 (i) selenium;
 (j) stromal-derived factor;
 (k) sodium pyruvate;
 (l) transferrin; and
 (m) serum free medium.

The stem cell growth medium may have more particular amounts of each component as follows:
 (a) serum (0.1 to about 50% by vol);
 (b) fibroblast growth factor (1 pg/ml to 100 ng/ml);
 (c) epidermal growth factor (1 pg/ml to 100 ng/ml);
 (d) hydrocortisone (1 pg/ml to 100 pg/ml);
 (e) calcium chloride (1 nM to 100 mM);
 (f) insulin (1 ng/ml to 100 mg/ml);
 (g) bovine pituitary extract (1 pg/ml to 100 mg/ml);
 (h) L-cysteine or glutathione (1 nM to 100 mM);
 (i) selenium (1 pg/ml to 100 mg/ml);
 (j) stromal-derived factor (1 pg/ml to 100 ng/ml);
 (k) sodium pyruvate (1 ng/ml to 100 mg/ml);
 (l) transferrin (1 ng/ml to 100 mg/ml); and
 (m) serum free medium (balance to 100% volume).

The stem cell growth medium may have more particular amounts of each component as follows:
 (a) serum (about 1 to about 10% by vol);
 (b) fibroblast growth factor (1 to about 10 ng/ml);
 (c) epidermal growth factor (1 to about 10 ng/ml);
 (d) hydrocortisone (about 10 about 100 ng/ml);
 (e) calcium chloride (0.01 to about 0.1 mM);
 (f) insulin (about 0.5 to about 5 mg/ml);
 (g) bovine pituitary extract (about 10 to about 100 µg/ml);
 (h) L-cysteine or glutathione (about 0.5 to about 5 mM);
 (i) selenium (about 0.1 to about 1 µg/ml);
 (j) stromal-derived factor (1 to about 10 ng/ml);

(k) sodium pyruvate (2 to about 20 mg/ml);
(l) transferrin (0.1 to about 1 mg/ml); and
(m) serum free medium (balance to 100% volume).

The stem cell growth medium may have more particular amounts of each component as follows:
(a) serum (about 5% by vol);
(b) fibroblast growth factor (about 2 ng/ml);
(c) epidermal growth factor (about 5 ng/ml);
(d) hydrocortisone (about 74 ng/ml);
(e) calcium chloride (about 0.9 mM);
(f) insulin (about 1 mg/ml);
(g) bovine pituitary extract (about 50 µg/ml);
(h) L-cysteine or glutathione (about 2 mM);
(i) selenium (about 0.67 µg/ml);
(j) stromal-derived factor (about 2 ng/ml);
(k) sodium pyruvate (about 11 mg/ml);
(l) transferrin (about 0.55 mg/ml); and
(m) serum free medium (balance to 100% volume).

The serum may be human serum or fetal bovine serum. One or both of FGF and or EGF may be recombinant FGF and/or EGF. The SDF-1 may be recombinant SDF-1. One or both of insulin and/or transferrin may be recombinant insulin and/or transferrin. The medium may contain L-cysteine. The medium may contain glutathione. The serum free medium is Keratinocyte-SFM, Defined Keratinocyte-SFM, MCDB 153, Keratinocyte Growth Medium, DMEM/F12, Ham's F10, Ham's F12 or RPMI 1640.

In another embodiment, there is provided a stem cell attachment medium comprising:
(a) serum;
(b) L-cysteine or glutathione;
(c) insulin;
(d) selenium;
(e) sodium pyruvate;
(f) transferrin; and
(g) low glucose-DMEM or α-MEM.

The stem cell attachment medium may have more particular amounts of each component as follows:
(a) serum (0.1 to about 50% by volume);
(b) L-cysteine or glutathione (1 nM to about 100 mM);
(c) insulin (1 ng/mL to about 100 mg/mL);
(d) selenium (1 pg/mL to about 100 mg/mL);
(e) sodium pyruvate (1 ng/mL to about 100 mg/mL);
(f) transferrin (1 ng/mL to about 100 mg/mL); and
(g) low glucose-DMEM or α-MEM (balance to 100% volume).

The stem cell attachment medium may have more particular amounts of each component as follows:
(a) serum (about 10% by volume);
(b) L-cysteine or glutathione (about 0.5 to about 5 mM);
(c) insulin (about 0.5 to about 5 mg/ml);
(d) selenium (about 0.1 to about 1 µg/ml);
(e) sodium pyruvate (about 2 to about 22 mg/ml);
(f) transferrin (about 0.1 to about 1 mg/ml); and
(g) low glucose-DMEM or α-MEM (balance to 100% volume).

The stem cell attachment medium may have the particular amounts of each component as follows:
(a) serum (about 10% by volume);
(b) L-cysteine or glutathione (about 2 mM);
(c) insulin (about 1 mg/ml);
(d) selenium (about 0.67 µg/ml);
(e) sodium pyruvate (about 11 mg/ml);
transferrin (about 0.55 mg/ml); and
(g) low glucose-DMEM or α-MEM (balance to 100% volume).

The medium may contain low-glucose DMEM. The medium may contain α-MEM. The medium may contain L-cysteine. The medium may contain glutathione. The serum may be is fetal bovine serum or human serum. One or both of insulin and/or transferrin may be recombinant insulin and/or transferrin.

In other embodiments, there are provided a method of culturing a cell in the stem cell growth medium as set forth above, and a method of culturing a cell in the stem cell attachment medium as set forth above. The cultured cell may be a multipotent stem cell. The multipotent stem cell may be is derived from adipose tissue. The multipotent stem cell may undergo clonal expansion. The multipotent stem cell may be growing attached to a plastic material, and/or showing spindle-shaped morphological features. The multipotent stem cell may be induced to undergo adipogenic differentiation, chondrogenic differentiation, or osteogenic differentiation. The multipotent stem cell may express immunologically detectable surface expression of responses to CD 73, CD 90 and/or CD105, and/or may express negative immunologically detectable surface expression of CD 34, CD 45 and/or HLA-DR.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 2. Proliferation comparison between presently disclosed media and well known manufacturer's media for using Ad-MSCs.

DETAILED DESCRIPTION

Figure 1:
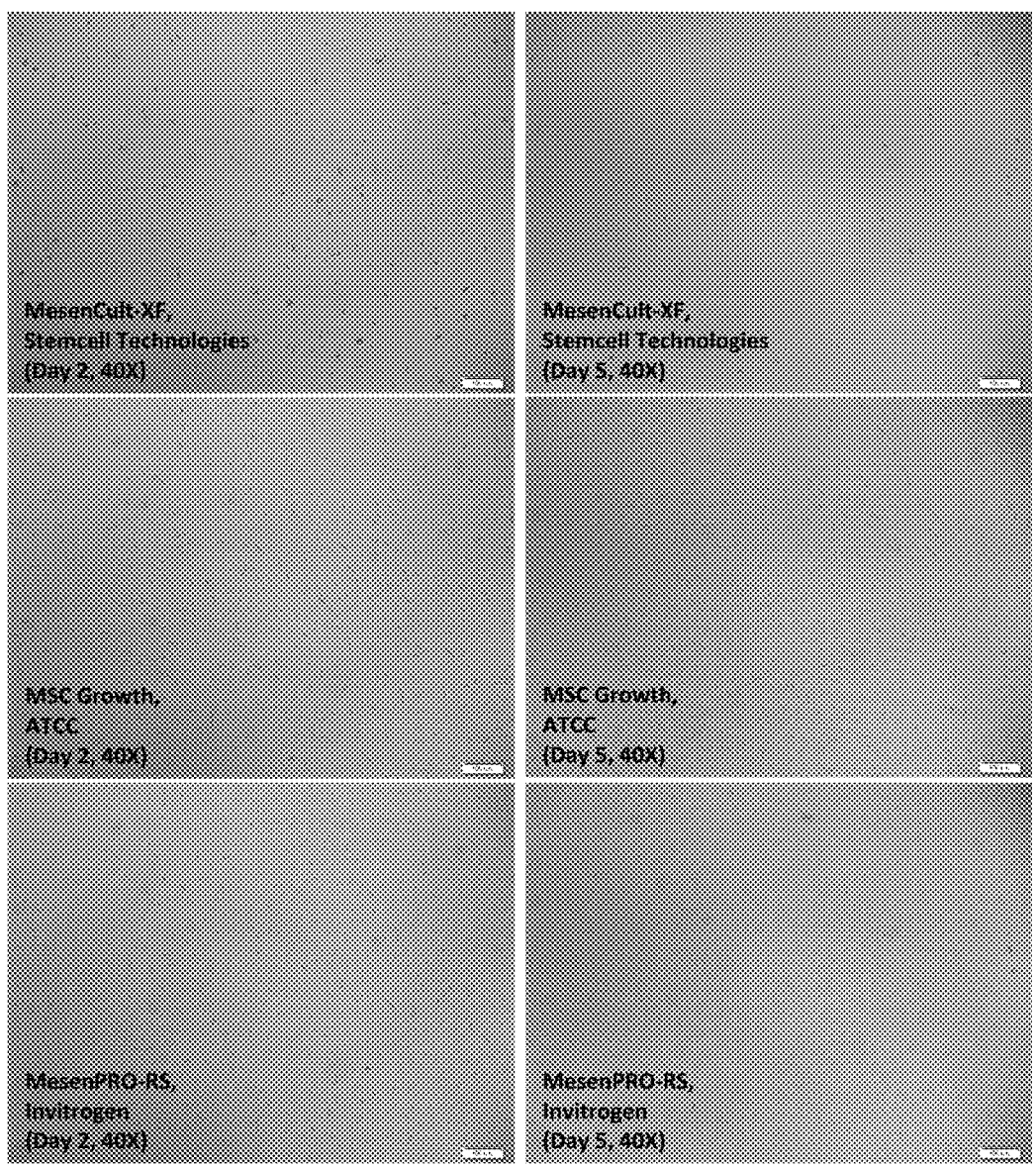
FIG. 1. Comparison of Ad-MSCs morphology between presently disclosed media and well known manufacturer's media for using Ad-MSCs.

The disclosure provides a culture medium for human adipose tissue derived mesenchymal stem cells includes a Keratinocyte-based growth medium, L-Cysteine, FGF and SDF-1. The culture medium is effective for growing mesenchymal stem cells at a high proliferation rate while maintaining the purity, characterization and undifferentiated state of the cells. The below described Ad-MSC expansion method and reagents were selected to allow for high expansion efficiencies from donors without measurable loss in safety profile, genetic stability, vitality, and differentiation potency, migration and homing characteristics of the MSCs.

I. Adipose Tissue

Adipose tissue, body fat, or simply fat is loose connective tissue composed mostly of adipocytes. In addition to adipocytes, adipose tissue contains the stromal vascular fraction (SVF) of cells including pre-adipocytes, fibroblasts, vascular endothelial cells and a variety of immune cells (i.e., adipose tissue macrophages, or ATMs). Adipose tissue is derived from pre-adipocytes. Its main role is to store energy in the form of lipids, although it also cushions and insulates the body. Far from hormonally inert, adipose tissue has, in recent years, been recognized as a major endocrine organ, as it produces hormones such as leptin, estrogen, resistin, and the cytokine TNFα. Moreover, adipose tissue can affect other organ systems of the body and may lead to disease. The two types of adipose tissue are white adipose tissue (WAT), which stores energy, and brown adipose tissue (BAT), which generates body heat. The formation of adipose tissue appears to be controlled in part by the adipose gene.

In humans, adipose tissue is located beneath the skin (subcutaneous fat), around internal organs (visceral fat), in bone marrow (yellow bone marrow), intermuscular (Muscular system) and in the breast tissue. Adipose tissue is found in specific locations, which are referred to as adipose depots. Apart from adipocytes, which comprise the highest percentage of cells within adipose tissue, other cell types are present, collectively termed stromal vascular fraction (SVF) of cells. SVF includes pre-adipocytes, fibroblasts, adipose tissue macrophages, and endothelial cells. Adipose tissue contains many small blood vessels. In the integumentary system, which includes the skin, it accumulates in the deepest level, the subcutaneous layer, providing insulation from heat and cold. Around organs, it provides protective padding. However, its main function is to be a reserve of lipids, which can be burned to meet the energy needs of the body and to protect it from excess glucose by storing triglycerides produced by the liver from sugars, although some evidence suggests that most lipid synthesis from carbohydrates occurs in the adipose tissue itself. Adipose depots in different parts of the body have different biochemical profiles. Under normal conditions, it provides feedback for hunger and diet to the brain.

Free fatty acids are liberated from lipoproteins by lipoprotein lipase (LPL) and enter the adipocyte, where they are reassembled into triglycerides by esterifying it onto glycerol. Human fat tissue contains about 87% lipids.

There is a constant flux of FFA (Free Fatty Acids) entering and leaving adipose tissue. The net direction of this flux is controlled by insulin and leptin. If insulin is elevated there is a net inward flux of FFA, and only when insulin is low can FFA leave adipose tissue. Insulin secretion is stimulated by high blood sugar, which results from consuming carbohydrates. In humans, lipolysis (hydrolysis of triglycerides into free fatty acids) is controlled through the balanced control of lipolytic B-adrenergic receptors and a2A-adrenergic receptor-mediated anti-lipolysis.

Fat cells have an important physiological role in maintaining triglyceride and free fatty acid levels, as well as determining insulin resistance. Abdominal fat has a different metabolic profile being more prone to induce insulin resistance. This explains to a large degree why central obesity is a marker of impaired glucose tolerance and is an independent risk factor for cardiovascular disease (even in the absence of diabetes mellitus and hypertension). Studies of female monkeys discovered that individuals suffering from higher stress have higher levels of visceral fat in their bodies. This suggests a possible cause-and-effect link between the two, wherein stress promotes the accumulation of visceral fat, which in turn causes hormonal and metabolic changes that contribute to heart disease and other health problems.

Recent advances in biotechnology have allowed for the harvesting of adult stem cells from adipose tissue, allowing stimulation of tissue regrowth using a patient's own cells. In addition, adipose-derived stem cells from both human and animals reportedly can be efficiently reprogrammed into induced pluripotent stem cells without the need for feeder cells. The use of a patient's own cells reduces the chance of tissue rejection and avoids ethical issues associated with the use of human embryonic stem cells. A growing body of evidence also suggests that different fat depots (i.e., abdominal, omental, pericardial) yield adipose-derived stem cells with different characteristics. These depot-dependent features include proliferation rate, immunophenotype, differentiation potential, gene expression, as well as sensitivity to hypoxic culture conditions.

Adipose tissue is the greatest peripheral source of aromatase in both males and females, contributing to the production of estradiol.

Adipose derived hormones include:
Adiponectin
Resistin
Plasminogen activator inhibitor-1 (PAI-1)
TNFα
IL-6
Leptin
Estradiol (E2)

Adipose tissues also secrete a type of cytokines (cell-to-cell signaling proteins) called adipokines (adipocytokines), which play a role in obesity-associated complications. Perivascular adipose tissue releases adipokines such as adiponectin that affect the contractile function of the vessels that they surround.

II. Growth Media

The components of the growth media are listed in Table 1.

TABLE 1

Component concentrations of growth media*

| Reagents | Component Ranges | A Preferred Embodiment |
|---|---|---|
| Keratinocyte-based cell growth media (Serum Free Medium) | Balance to 100% vol | Balance to 100% vol |
| FBS (Fetal Bovine Serum) | 0.1~50% vol | ~10% vol |

TABLE 1-continued

Component concentrations of growth media*

| Reagents | Component Ranges | A Preferred Embodiment |
|---|---|---|
| Acidic-FGF (Fibroblast Growth Factor) or Basic-FGF (Fibroblast Growth Factor) | 1 pg/mL~100 ng/mL | 1~10 ng/mL |
| EGF (Epidermal Growth Factor) | 1 pg/mL~100 ng/mL | 1~10 ng/mL |
| Hydrocortisone | 1 pg/mL~100 µg/mL | 10~100 ng/mL |
| Calcium Chloride | 1 nM~100 mM | 0.01~0.1 mM |
| Insulin | 1 ng/mL~100 mg/mL | 0.5~5 mg/mL |
| BPE (Bovine Pituitary Extract) | 1 pg/mL~100 mg/mL | 10~100 µg/mL |
| L-Cysteine or Glutathione | 1 nM~100 mM | 0.5~5 mM |
| Selenium | 1 pg/mL~100 mg/mL | 0.1~1 µg/mL |
| SDF-1 (Stromal cell-derived Factor) | 1 pg/mL~100 ng/mL | 1~10 ng/mL |
| Sodium Pyruvate | 1 ng/mL~100 mg/mL | 2~20 mg/mL |
| Transferrin | 1 ng/mL~100 mg/mL | 0.1~1 mg/mL |

To make the disclosed cell growth media, combine all of the ingredients listed in Table 1 at their respective concentrations with the basal media. All of the powder form ingredients need to be dissolved in a salt buffered solution such as distilled deionized water (DDW), phosphate buffered saline (PBS), Dulbecco's phosphate buffered solution (DPBS), Hanks' Balanced Salt Solution (HBSS), Earle's Balanced Salt Solution (EBSS) etc. To use the ingredients, prepare the stock solutions at 100-1000 times the needed concentration. Each stock solution should then be filtered using a 0.1 µm filter. The filtered stock solutions should be stored at either room temperature or refrigerated temperature (2-8° C.) or freezing (−20° C.).

There are instances where the disclosed ingredients can be substituted. For example, in lieu of FBS, human serum may be substituted. In autologous cell therapy, one's own serum may be used during cell culture. Also, instead of animal based proteins, recombinant proteins may be used. For example, instead of b-FGF, recombinant b-FGF can be used. Likewise, recombinant EGF can be used in lieu of EGF and recombinant SDF-1 can be used instead of SDF-1.

All of the stock solutions and supplements are combined with the basal medium to create the disclosed growth media. The final product should be used immediately or stored in a refrigerator (2-8° C.) to maintain optimal quality.

III. Adipose Tissue Harvest

There are two methods of isolation: from solid fat blocks after surgery or from liposuction aspirate. Both methods harvest MSCs with similar quantities and in equal ratios. Liposuction is considered to be the easiest, safest and fastest way to harvest MSCs. For the liposuction aspirate, a cannula connected to a syringe is used to carefully extract the fat. Approximately 1-20 mL of compact fat is needed for this process. Three ml or more is the preferred amount. Harvested fat should be stored at 2-8° C. for no more than 72 hours to maintain optimal MSC isolation.

MSC Isolation is performed as follows. Harvested fat tissue is transferred into 10 cc aseptic syringes, which are centrifuged at 3100 rpm for 3 minutes. After centrifugation, there should be 3 layers. The top is the oil layer, the middle is compact fat and the bottom contain all the solutions such as tumescent solution and blood. The top and bottom layers are discarded, leaving just the middle, compact fat layer, which is transferred into a 50 mL conical tube. The collagenase type I solution is prepared by dissolving the collagenase powder into low glucose-DMEM or alpha-MEM at a concentration of 1 mg/mL. Four 4 mL of collagenase type I solution is added per 1 mL of fat, which is then placed into a shaking incubator at 37° C., 150+/−30 rpm for 1~2 hours.

After enzyme digestion is complete, the samples are centrifuged at 1800 rpm for 5 minutes. After centrifugation, two layers will be present and the top layer is discarded. The bottom layer is resuspended with the disclosed attachment media as listed in Table 2. Although the disclosed attachment media is the preferred media, any commercially available cell attachment media may be used. To remove any debris, a 100 µm cell strainer is used to filter the material. The samples are centrifuged at 1700 rpm for 5 minutes, which will result in a cell pellet otherwise known as stromal vascular fraction (SVF).

TABLE 2

Component concentrations of attachment media

| Reagents | Component Ranges | A Preferred Embodiment |
|---|---|---|
| Low glucose-DMEM or α-MEM | Balance to 100% vol | Balance to 100% vol |
| FBS (Fetal Bovine Serum) | 0.1~50% vol | ~10% vol |
| L-Cysteine or Glutathione | 1 nM~100 mM | 0.5~5 mM |
| Insulin | 1 ng/mL~100 mg/mL | 0.5~5 mg/mL |
| Selenium | 1 pg/mL~100 mg/mL | 0.1~1 µg/mL |
| Sodium Pyruvate | 1 ng/mL~100 mg/mL | 2~20 mg/mL |
| Transferrin | 1 ng/mL~100 mg/mL | 0.1~1 mg/mL |

The cell pellet is seeded on a culture flask using the disclosed attachment media. The size of the culture flask depends on the amount of compact fat. For fat volume greater than 2 ml, a T75-flask should be used. For fat volume equal or less than 2 ml, a T25-flask should be used. The seeded flask is then placed in a $CO_2$ incubator at 5% $CO_2$ and 37° C. for 16~32 hours.

IV. Msc Expansion

After the 16~32 hour incubation period, the user should confirm that the cells have attached using an inverted microscope. All non-adherent cells, such as red blood cells, white blood cells, macrophages and pre-adipocytes, etc., are discarded. The culture flask is washed with PBS or DPBS, two times and the disclosed growth media (For T75-flask 10~15 mL and for T25-flask 3~7 mL) is added to the flask to achieve the first expansion passage or P0. The flask is placed into an incubator at 5% $CO_2$ and 37° C. The disclosed growth media is changed every 2 days. When 90% confluence is achieved, the old media is discarded and the flask and washed once with PBS or DPBS (for T75-flask 5~7 mL and for T25-flask 3~5 mL). TrypLE™ Select solution (Life Technologies) is added to the flask (For T75-flask 3 mL and for T25-flask 1 mL) and incubated at 5% $CO_2$ and 37° C. for 3 minutes. Once cells are confirmed to be detached from the bottom of the flask, PBS or DPBS is added at the same amount as the TrypLE™ Select solution to neutralize the enzyme. A small sample is taken to count the cell number. The remaining cells are centrifuged at 1700 rpm for 5 minutes, and the supernatant is discarded, leaving the cell pellet. According to the desired cell number or use, the cells are divided for subculture to P1 or cryopreservation.

For subculture to P1, the cells are resuspended in the disclosed growth media. When seeding a T175 flask, at least $1.5 \times 10^6$ cells are required and a Triple-flask will need at least $4.5 \times 10^6$ cells. The amount of disclosed growth media used will also depend on flask size. For a T175-flask, 24~30 mL is used and for a Triple-flask, 90~100 mL is used. This subculture process may be repeated to achieve the desired cell amounts.

For cryopreservation, the cells are resuspended with a freezing solution comprised of disclosed growth media and 10% Dimethyl Sulfoxide (DMSO). $1.0 \times 10^6$~$1.0 \times 10^7$ cells/mL are transferred into each cryovial. Using a controlled rate freezer (CRF), the cells are slowly cryopreserved. When complete, the cells are transferred to vapor type liquid nitrogen storage tank for indefinite storage.

Cryopreserved cells can be thawed and sub-cultured using the same method above. When thawing, the cryovials are placed in a 37° C. water bath for less than 2 minutes. After thawing, the cells are transferred to a 50 mL conical tube containing 9 mL of the disclosed growth media and centrifuged at 1700 rpm for 5 minutes. After centrifugation, the top layer is discarded and the cells re-suspend with disclosed growth media. The cells are seeded onto the appropriate culture flasks.

V. Examples

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Methods

Proliferation comparison. After harvesting MSCs, MSCs are seeded into culture vessels at $1 \times 10^6$ cells/T75 flask with MesenCult-XF media (STEMCELL Technologies Inc.), MSC Growth media (ATCC), MesenPRO-RS (Invitrogen), MSC Growth media (Cell Applications Inc.), Bulletkit-ADSC media (Lonza), Stemline MSC Expansion media (Sigma-Aldrich), or the growth media disclosed here, to a total of 8 T75-flasks. The cells can be incubated at 37° C. in 5% $CO_2$. All media will be changed approximately every 2 days.

For morphology and cell proliferation comparison, pictures are taken at day 2 and day 5, and the number of cells is counted by trypan blue dye exclusion method at day 5.

Adipogenic differentiation induction of expanded MSCs. After harvesting MSCs, MSCs are seeded into culture vessels at $1 \times 10^4$ cells/cm$^2$. For classical stain differentiation assay, cells are seeded into a multi-well plate. The cells are incubated in this growth media at 37° C. in 5% $CO_2$ for a minimum of 2 hours up to 4 days.

Media is replaced with Complete Adipogenesis Differentiation Medium and continue incubation. MSCs will continue to undergo limited expansion as they differentiate under adipogenic conditions. Cultures are re-fed every 3~4 days.

After specific periods of cultivation, adipogenic cultures can be processed for Oil Red 0 staining (beginning at 7~14 days).

Chondrogenic differentiation induction of expanded MSCs. After harvesting MSCs, the cell pellet is resuspended in an appropriate volume of new growth media to generate a cell solution of $1.6 \times 10^7$ viable cells/mL.

Micromass cultures are generated by seeding 5 µL droplets of cell solution in the center of multi-well plate wells for classical staining.

After cultivating micromass cultures for 2 hours high humidity conditions, Complete Chondrogenesis Medium is added to culture vessels and incubated in 37° C. incubator with 5% $CO_2$ Cultures are re-fed every 2~3 days.

After specific periods of cultivation, chondrogenic pellets can be processed for Toluidine Blue O staining (>14 days).

Osteogeneic differentiation induction of expanded MSCs. After harvesting MSCs, MSCs are seeded into culture vessels at $5 \times 10^3$ cells/cm$^2$. For classical stain differentiation assay, cells are seeded into a multi-well plate. The cells are seeded in new growth media at 37° C. in 5% $CO_2$ for a minimum of 2 hours up to 4 days.

Media is replaced with Complete Osteogenesis Differentiation Medium and incubation continued. MSCs will continue to expand as they differentiate under osteogenic conditions. Cultures are re-fed every 3~4 days.

After specific periods of cultivation, osteogenic cultures can be processed for Alizarin Red S staining (>21 days).

Immunological characteristic analysis of expanded MSCs. One of the problems with ex vivo expansion of stem cells is decrease in quality and cell characteristics over many passages. Thus, the expanded Ad-MSC will also undergo a surface antigen analysis to determine retained stem cell characteristics. Ad-MSC express CD73, CD90, and CD105 but lack expression of the hematopoietic lineage markers, CD34, CD45, and human leukocyte antigen-DR. The surface antigens will be tested using flow cytometry.

The cells will be washed with PBS and treated with TrypLE™ Select before being centrifuged at 1700 rpm for 5 minutes. The supernatant will be discarded and the MSC pellet will be wash with 2% FBS or human serum and PBS before being centrifuged again. The supernatant will again be removed and discarded. The cells will be suspended in PBS and mixed with an antibody, FITC (fluorescein isothiocyanate), PE (phycoerythrin), APC (allo-phycocyanin), APC/Cy7, PerCP-Cy5.5, Brilliant Violet 421, etc. The cells/antibody mixture will be incubated on ice for at least 40 min before being centrifuged for 5 minutes, followed by the PBS wash step. The final cell pellet can be fixed with 1% paraformaldehyde and introduced into the flow cytometer.

In the flow cytometer, the cells will pass single-file through a laser beam as the cytometer records how the cells scatter the incident light and emit fluorescence. This will allow for analysis of the surface molecule at the single-cell level.

TABLE 3

FACS analysis of surface antigens of adipose-derived mesenchymal stem cells

| Antigen | Ad-MSCs |
|---|---|
| CD34 | − |
| CD45 | − |
| CD73 | + |
| CD90 | + |
| CD105 | + |
| HLA-DR | − |

Example 2

Results

Morphology and Proliferation comparison. Ad-MSCs of all culture conditions displayed a characteristic fibroblast-like morphology at day 2. However, cells cultured by the disclosed growth media appeared smaller and more homogeneous spindle fibroblast-like morphology in comparison to other well-known manufacturer's media at day 5. Also at day 5, the confluency of Ad-MSCs cultured by the disclosed growth media observed much higher than other well-known manufacturer's media (FIG. 1). As shown in FIG. 2, between days 0 and 5, the proliferation rate of Ad-MSCs cultured by the disclosed media was 2 to 10 times higher than other well-known manufacturer's media.

Figure 3:
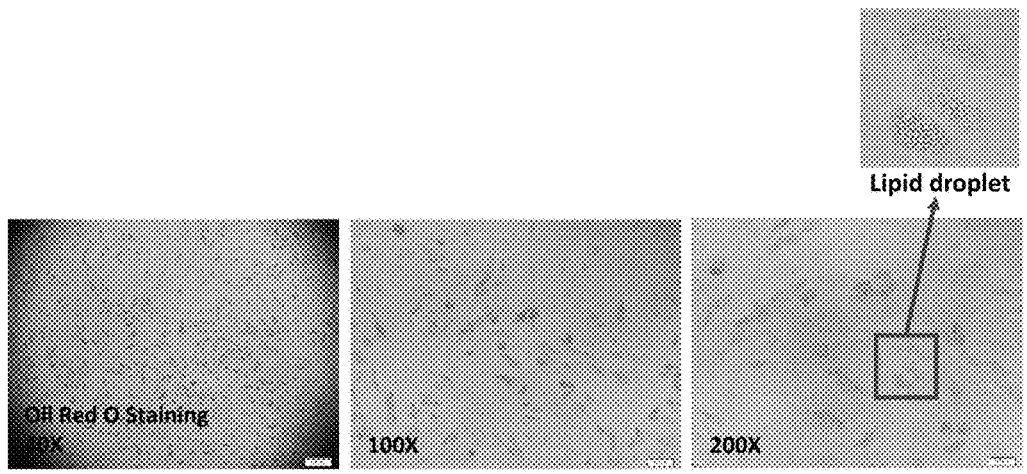
FIG. 3. Adipogenic differentiation induction of Ad-MSCs cultured by the disclosed growth media.
Figure 4:
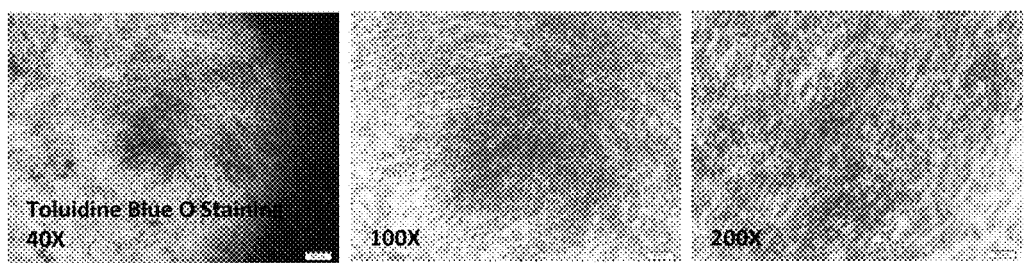
FIG. 4. Chondrogenic differentiation induction of Ad-MSCs cultured by the disclosed growth media.
Figure 5:
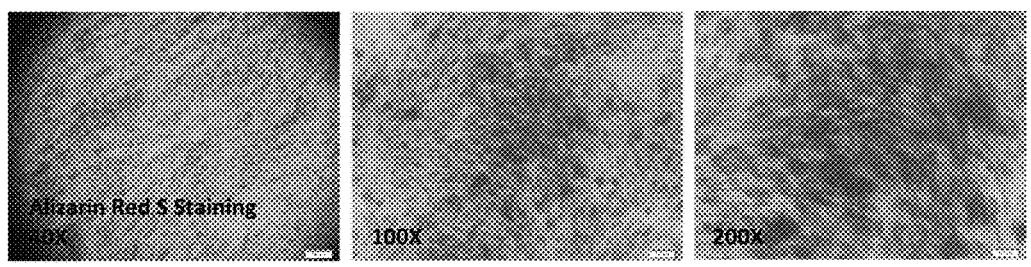
FIG. 5. Osteogenic differentiation induction of Ad-MSCs cultured by the disclosed growth media.

Multilineage differentiation induction of expanded MSCs. The multilineage differentiation capability of Ad-MSCs was examined by culturing cells collected under condition favorable for adipogenic, chondrogenic, and osteogenic differentiation. Adipogenesis and lipid vacuole formation in the MSCs were studied by staining cells with Oil Red O. At day 14 post adipogenic inductions, MSCs contained large Oil Red O positive lipid droplets within their cytoplasm (FIG. 3). Chondrogenesis in MSCs was confirmed by staining chondrogenic proteoglycan (GAG, glycosaminoglycan) with Toluidine Blue O. At day 14 post chondrogenic inductions, chondrogenesis was characterized by the presence of strongly stained Toluidine Blue O positive. Osteogenesis in MSCs was stained with Alizarin Red S to determine calcium deposition. The cellular morphology changed from spindle shape to cuboid shape. At day 21 post osteogenic inductions, high level of osteogenesis was characterized by the presence of strongly stained Alizarin Red S positive nodular structures with well-defined inter-nodular regions not containing cells (FIG. 5).

Figure 6:
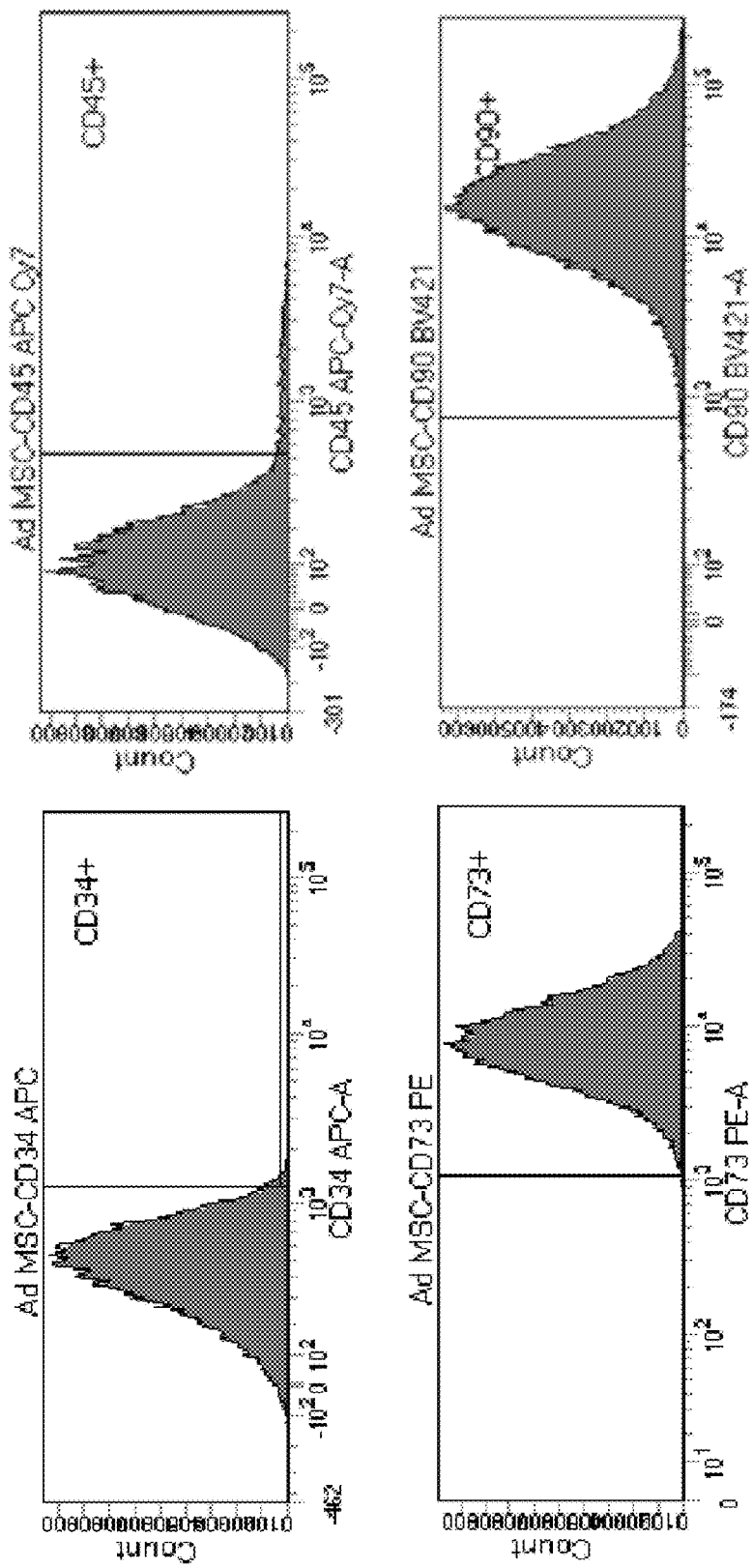
FIG. 6. FACS analysis of Ad-MSCs cultured by the disclosed growth media.

Immunological characteristic analysis of expanded MSCs. The expression of cell surface markers was analyzed by flow cytometry. All Ad-MSCs were highly positive for mesenchymal stromal cells surface markers including CD73 (99.25%), CD90 (98.88%), and CD105, and were negative for the hematopoietic and endothelial markers including CD34 (1.29%), CD45 (6.39%), and HLA-DR (1.57%) (FIG. 6).

* * *

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. References

The following references, to the extent that they provide exemplary procedural or other details supplementary to those set forth herein, are specifically incorporated herein by reference.

U.S. Pat. No. 7,807,461
U.S. Patent Publication 20130089928
WO2013032052
WO2007123363
Colleoni et al., *Vet Res Commun.* 33(8):811-21 (2009).
Furge et al., Oncogene 19:5582-5589 (2000).
Krampera et al., *Blood,* 106:59-66 (2005).
Kang et al., *J Cell Biochem* 95: 1135-1145 (2005).
Pons et al., *Biochem Biophys Res Commun* 376:419-422 (2008).
Sen et al., *J Cell Biochem* 81:312-319 (2001).
Tamama et al., *Stem Cells,* 24:686-695 (2006).
Tamama et al., *J Biomed Biotechnol* 10.1155/2010/795385 (2010).
Wagner et al., Replicative Senescence of Mesenchymal Stem Cells: A Continuous and Organized Process. Zwaka T, ed. *PLoS ONE.* 3(5):e2213 (2008).

What is claimed:

1. A stem cell growth medium comprising:
   (a) serum about 1% to about 10% by volume;
   (b) fibroblast growth factor 1 to about 10 ng/ml;
   (c) epidermal growth factor 1 to about 10 ng/ml;
   (d) hydrocortisone about 10 to about 100 ng/ml;
   (e) calcium chloride 0.01 to about 0.1 mM;
   (f) insulin about 0.5 to about 5 mg/ml;
   (g) bovine pituitary extract about 10 to about 100 µg/ml;
   (h) L-cysteine or glutathione about 0.5 to about 5 mM;
   (i) selenium about 0.1 to about 1 µg/ml;
   (j) stromal-derived factor 1 to about 10 ng/ml;
   (k) sodium pyruvate 2 to about 20 mg/ml;
   (l) transferrin 0.1 to about 1 mg/ml; and
   (m) serum free medium balance to 100% volume.

2. The stem cell growth medium of claim 1, wherein the serum is human serum.

3. The stem cell growth medium of claim 1, wherein the serum is fetal bovine serum.

4. The stem cell growth medium of claim 1, wherein at least one of the FGF or the EGF is recombinant.

5. The stem cell growth medium of claim 1, wherein the SDF is recombinant SDF.

6. The stem cell growth medium of claim 1, wherein at least one of the insulin or the transferrin is recombinant.

7. The stem cell growth medium of claim 1, wherein said medium contains L-cysteine.

8. The stem cell growth medium of claim 1, wherein said medium contains glutathione.

9. The stem cell growth medium of claim 1, wherein the serum free medium is Keratinocyte-SFM, Defined Keratinocyte-SFM, MCDB 153, Keratinocyte Growth Medium, DMEM/F12, Ham's F10, Ham's F12 or RPMI 1640.

10. A method of culturing a cell, the method comprising culturing the cell in the stem cell growth medium of claim 1.

11. The method of claim 10, wherein said cell is a multipotent stem cell.

12. The method of claim 11, wherein said multipotent stem cell is derived from adipose tissue.

13. The method of claim 11, wherein said multipotent stem cell undergoes clonal expansion.

14. The method of claim 11, wherein said multipotent stem cell is growing attached to a plastic material, showing spindle-shaped morphological features.

15. The method of claim 11, wherein said multipotent stem cell is induced to undergo adipogenic differentiation.

16. The method of claim 11, wherein said multipotent stem cell is induced to undergo chondrogenic differentiation.

17. The method of claim 11, wherein said multipotent stem cell is induced to undergo osteogenic differentiation.

18. The method of claim 11, wherein said multipotent stem cell expresses immunologically detectable surface expression of responses to CD73, CD90 or CD105, and/or expresses negative immunologically detectable surface expression of CD34, CD45 or HLA-DR.

19. A kit comprising ingredients for preparation of the stem cell growth medium according to claim 1.

\* \* \* \* \*